United States Patent
Su et al.

(10) Patent No.: US 10,577,404 B2
(45) Date of Patent: Mar. 3, 2020

(54) POLYPEPTIDE DERIVATIVES FROM GRASS CARP INTERFERON AND APPLICATION THEREOF

(71) Applicant: Huazhong Agricultural University, Wuhan, Hubei (CN)

(72) Inventors: Jianguo Su, Hubei (CN); Xun Xiao, Hubei (CN); Wentao Zhu, Hubei (CN)

(73) Assignee: Huazhong Agricultural University, Wuhan (CN)

(*) Notice: Subject to any disclaimer, the term of this patent is extended or adjusted under 35 U.S.C. 154(b) by 0 days.

(21) Appl. No.: 16/419,944

(22) Filed: May 22, 2019

(65) Prior Publication Data

US 2019/0359673 A1    Nov. 28, 2019

(30) Foreign Application Priority Data

May 23, 2018 (CN) .......................... 2018 1 0503117

(51) Int. Cl.
  *C07K 14/555* (2006.01)
  *A61P 31/04* (2006.01)

(52) U.S. Cl.
  CPC ............ *C07K 14/555* (2013.01); *A61P 31/04* (2018.01)

(58) Field of Classification Search
  CPC ........ C07K 14/555; A61P 31/04; A61K 38/00
  See application file for complete search history.

(56) References Cited

U.S. PATENT DOCUMENTS 8,936,782 B2    1/2015    Cedars-Sinai Medical Center

FOREIGN PATENT DOCUMENTS

CN    102021175    * 11/2010  ............. C12N 15/21
CN    102021175 A    4/2011

OTHER PUBLICATIONS

Molecular characterization and transcription regulation analysis of type I IFN gene in grass carp (*Ctenopharyngodon idella*). Gene, 2012, vol. 504, pp. 31-40. (Year: 2012).*
CN102021175 translation to English, accessed online from patents.google.com on Aug. 7, 2019. (Year: 2010).*
Amber Kaplan et al., "Direct antimicrobial activity of IFN-β," Journal of Immunology, doi:10.4049/jimmunol.1601226, pp. 1-10 (Apr. 14, 2017).

* cited by examiner

Primary Examiner — Marcela M Cordero Gracia
(74) Attorney, Agent, or Firm — Mei & Mark LLP; Manni Li

(57) ABSTRACT

Derivative polypeptide derived from a grass carp interferon and an application of the derivative polypeptide. An amino acid sequence of the derivative polypeptide is as shown in SEQ ID NO:1; the interferon-derived polypeptide has a high-efficiency antibacterial effect and can take effect against drug-resistant *Escherichia coli, Staphylococcus aureus, Pseudomonas aeruginosa, Streptococcus agalactiae, Vibrio fluvialis* or *Aeromonas hydrophila*. The interferon-derived polypeptide is less toxic to eukaryotes and can effectively reduce the mortality of mice in a mouse disease model caused by pathological bacteria. The interferon-derived polypeptide which is small in molecular weight is easily synthesized and has a good application value.

4 Claims, 2 Drawing Sheets

Specification includes a Sequence Listing.

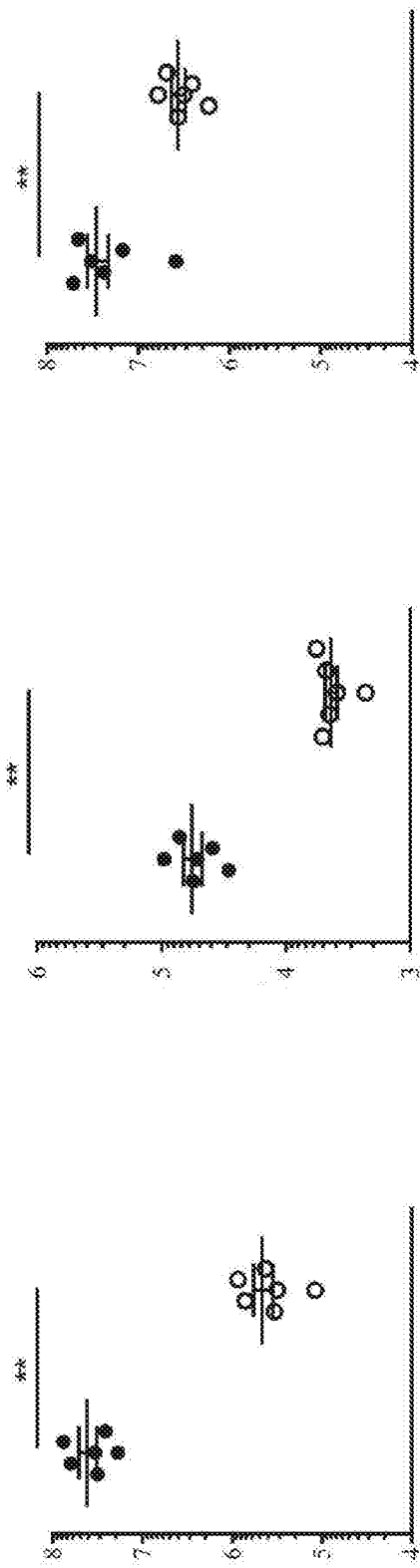
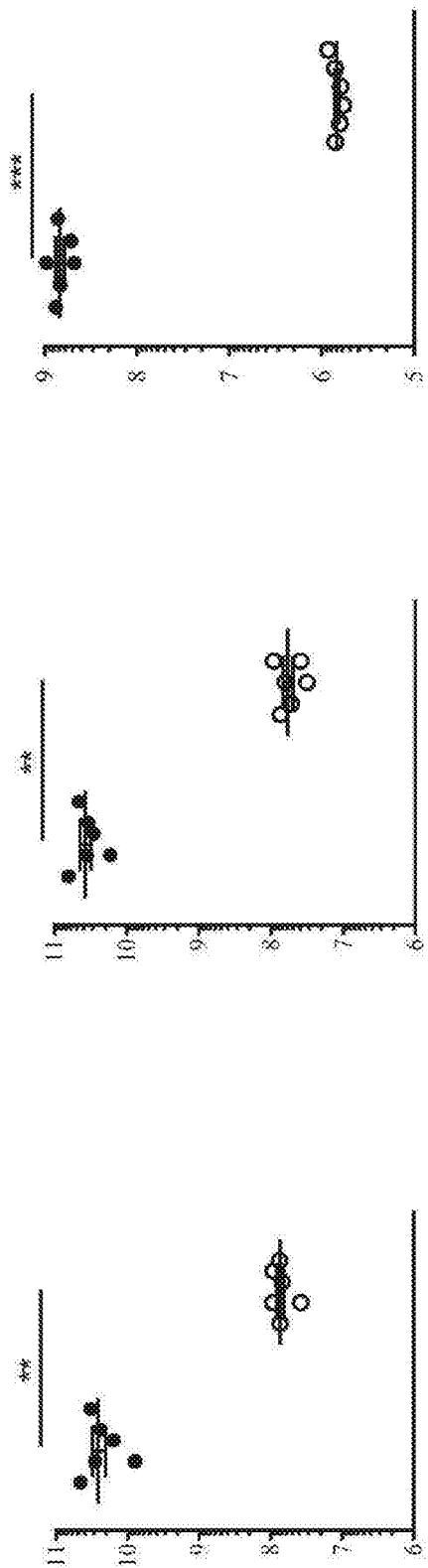

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: polypeptide derivative

<400> SEQUENCE: 1

-continued

```
Ser Tyr Glu Lys Lys Ile Asn Arg His Phe Lys Ile Leu Lys Lys Asn
1               5                   10                  15

Leu Lys Lys Lys
            20
```

POLYPEPTIDE DERIVATIVES FROM GRASS CARP INTERFERON AND APPLICATION THEREOF

CROSS-REFERENCE TO RELATED APPLICATIONS

The subject application claims priority on Chinese application no. CN 201810503117.X filed on May 23, 2018. The contents and subject matters of the Chinese priority application is incorporated herein by reference.

REFERENCE TO SEQUENCE LISTING

The official copy of the Sequence Listing is submitted concurrently with the specification as an ASCII formatted text file via EFS-Web, with a file name of "SequenceListing8006wh_ST25.txt", a creation date of May 22, 2019, and a size of 595 bytes. The Sequence Listing filed via EFS-Web is part of the specification and is incorporated in its entirety by reference herein.

BACKGROUND OF THE INVENTION

Technical Field

The present invention belongs to the field of biotechnology, and particularly relates to a derivative polypeptide derived from a grass carp interferon and an application thereof.

Description of Related Art

Traditional antibiotics have made certain achievements in the treatment of bacterial infections in the past few decades; however, in recent years, especially in the breeding industry, due to the abuse of antibiotics, more and more pathogenic microorganisms have developed resistance to traditional antibiotics, and the emergence of "superbacteria" has created a huge threat to human health and the development of aquaculture. Therefore, the development of a novel drug is of great significance and value.

Interferons are a type of secretory cytokines that play a major role in antiviral capability and immunoregulation in the body. Grass carp IFN1 belongs to the interferon family of proteins, which also includes IFN2, IFN3, IFN4, and IFNγ.

BRIEF SUMMARY OF THE INVENTION

In the present invention, it has been found that IFN1 has direct bactericidal function similar to antimicrobial peptides, in addition to the above functions. The tertiary structure of grass carp IFN1 protein is mainly composed of six α-helix short peptides. By artificially synthesizing polypeptides of different helical segments, amino acids at positions 107-127 of grass carp IFN1 have been shown to have a direct bactericidal function. Moreover, by in-vitro cytotoxicity assay, the toxicity of the peptide is significantly lower than that of the human antimicrobial peptide LL37. Compared with the grass carp IFN1 protein, the grass carp IFN1 derived polypeptide of the present invention has a smaller molecular weight, does not cause an antibody reaction after being directly injected into a mammalian body, and thus has a certain cross-border research value. Studies have shown that a variety of antibacterial protein-derived peptides have good application prospects.

An objective of the present invention is to provide a derivative polypeptide derived from a grass carp interferon having an amino acid sequence shown in SEQ ID NO: 1.

Another objective of the present invention is to provide an application of the derivative polypeptide derived from the grass carp interferon.

In order to achieve the objectives, the present invention provides a derivative polypeptide derived from a grass carp interferon, derived from a grass carp IFN1 protein sequence and having an amino acid sequence shown in SEQ ID NO:1, and a nucleotide sequence encoding the sequence shown in SEQ ID NO: 1 which also falls within the scope of the present invention.

The present invention also provides an application of a derivative polypeptide derived from a grass carp interferon, including preparing, by using the derivative polypeptide provided by the present invention, a bacterial inhibitor or a drug for treating or preventing a disease caused by a bacterial infection. In the application of the present invention, the bacteria include, but are not limited to, drug-resistant *Escherichia coli, Pseudomonas aeruginosa, Staphylococcus aureus, Streptococcus agalactiae, Vibrio fluvialis* or *Aeromonas hydrophila*.

The present invention provides a method for treating or preventing a disease caused by a bacterial infection, comprising the step of injecting into an animal a drug of which an active component or one of the active components is of a sequence shown in SEQ ID NO:1. In the method of the present invention, the bacteria include, but are not limited to, drug-resistant *Escherichia coli, Pseudomonas aeruginosa, Staphylococcus aureus, Streptococcus agalactiae, Vibrio fluvialis* and *Aeromonas hydrophila*.

The present invention further provides a method for inhibiting bacteria, comprising the steps of directly administering to bacteria a drug of which an active component or one of the active components is of a sequence shown in SEQ ID NO:1. In the method of the present invention, the bacteria include, but are not limited to, drug-resistant *Escherichia coli, Pseudomonas aeruginosa, Staphylococcus aureus, Streptococcus agalactiae, Vibrio fluvialis* and *Aeromonas hydrophila*.

Compared with the prior art, the present invention has the following advantages:

The interferon-derived polypeptide provided by the present invention is an interferon-derived polypeptide derived from the grass carp IFN1 protein sequence. The interferon-derived polypeptide has an efficient antibacterial effect and can function against porcine multi-drug resistant bacteria. The interferon-derived polypeptide is less toxic to eukaryotes and can effectively reduce the mortality of mice in a mouse disease model caused by pathological bacteria. Being small in molecular weight, the interferon-derived polypeptide is easily synthesized and has a good application value. For example, it may be used as a drug for treating bacterial diseases.

BRIEF DESCRIPTION OF THE SEVERAL VIEWS OF THE DRAWINGS

FIGS. 2A to 2F collectively show analysis of experimental results of the bacterial load of the derivative peptide of the present invention (SEQ ID NO:1) in different organs in mice, among which, FIG. 2A shows the results in lungs;

FIG. 2B shows the results in brains; FIG. 2C shows the results in kidneys; FIG. 2D shows the results in livers; FIG. 2E shows the results in spleens; and FIG. 2F shows the results in blood. In all the FIGS. 2A to 2F, the vertical axis has a unit of log CFU/ml, and along the horizontal axis, results with *E. coli*/PBS correspond to the cluster of solid black circles (with sold black color therein) and results with *E. coli*/helixE correspond to the cluster of circles in black line (with white space therein).

DETAILED DESCRIPTION OF THE INVENTION

Figure 1:
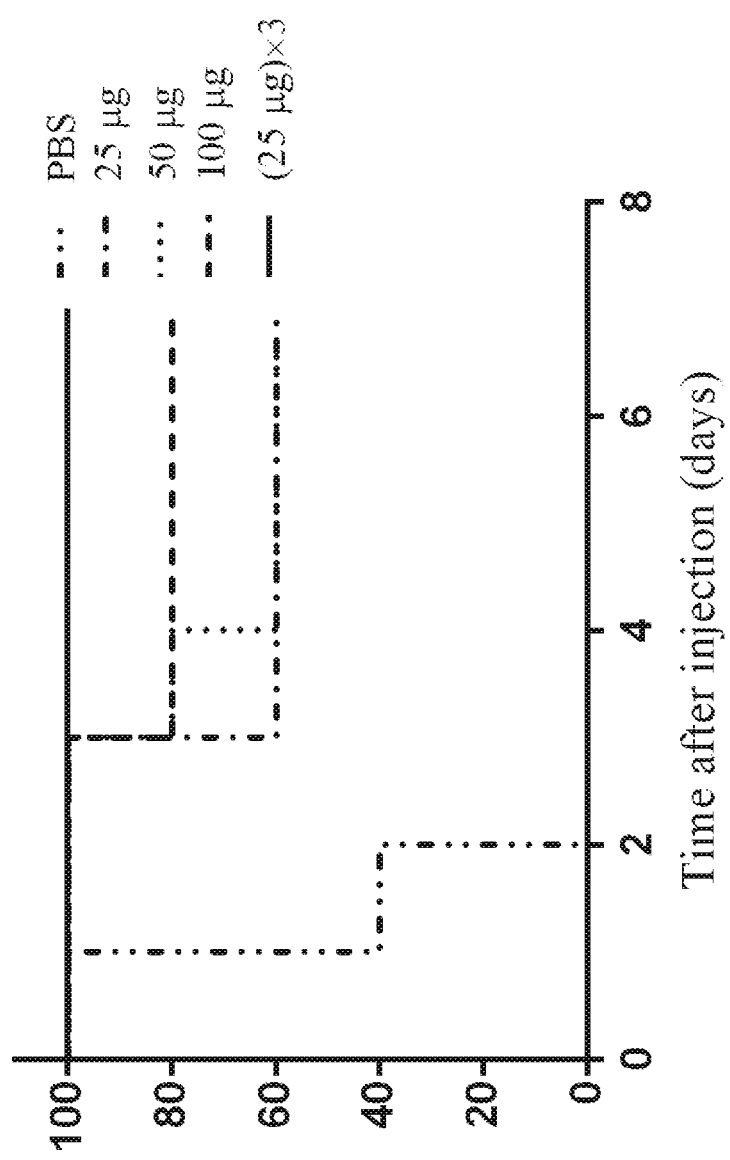
FIG. 1 shows the results of in vivo sterilization experiments of the interferon-derived polypeptide (SEQ ID NO:1) of the present invention; vertical axis shows percentage of survival.

The application of the interferon-derived polypeptide of the present invention is specifically illustrated by the following embodiments. These embodiments are only illustrative of the present invention and are not intended to limit the present invention. The technical solutions of the present invention, unless otherwise specified, are all conventional means in the art, and can be referenced to the "Microbiology Experiment" (Fourth Edition).

The derivative polypeptide having an amino acid sequence of SYEKKINRHFKILKKNLKKK, identified as SEQ ID NO:1 as used in the embodiments of the present invention, is artificially synthesized, and derivatized polypeptides obtained by eukaryotic expression in a conventional manner in the art also may implement the present invention.

Embodiment 1. Synthesis of the Derivative Peptide Derived from a Grass Carp Interferon of the Present Invention The derivative polypeptide of SEQ ID NO: 1 of the present invention is synthesized and provided by GenScript (Nanjing) Co., Ltd., and has a purity of more than 95%. Human antibacterial peptide LL37 is purchased from GenScript (Nanjing) Co., Ltd.

Embodiment 2. Antibacterial Activity Test

Test bacteria: *Vibrio fluvialis, Aeromonas hydrophila, Streptococcus agalactiae, Staphylococcus aureus, Pseudomonas aeruginosa*, pathogenic multi-drug resistant *Escherichia coli* PCN033 (Genome analysis and in vivo virulence of porcine extraintestinal pathogenic *Escherichia coli* strain PCN033). Specific steps are as follows:

(1) Six bacteria stored at −80° C.: *Vibrio fluvialis, Escherichia coli, Aeromonas hydrophila, Staphylococcus aureus, Pseudomonas aeruginosa, Streptococcus agalactiae*, are first melted at 4° C., and then taken out to reach room temperature, and then activated in a small amount of broth liquid medium respectively, and cultured in an incubator shaker at 30° C. for 18 hours to enter a logarithmic growth phase.

(2) The activated bacterial solution is inoculated on a broth-agar solid slant medium, and cultured in the incubator shaker at 30° C. for 18 hours and the lawn is then washed with sterile water and the bacterial solution is diluted to $5\times10^6$ CFU/ml.

(3) 10 µl of the diluted bacterial solution is mixed with 10 µl of polypeptide solutions of different concentrations of 1.0 mg/ml-0.001 mg/ml, and the mixture is then incubated in a constant-temperature water bath at 30° C. for 2 hours, 10 µl of the mixed solution is taken out for LB plate coating, and three parallels are prepared for each group; then, inverted incubation is carried out for 12 hours at 30° C., and colonies are counted and photographed. The negative control is bacterial solution+sterile water.

(4) The antibacterial rate is calculated according to a formula as follows:

Antibacterial rate (100%)=(colony count of negative control−colony count of experimental group)/colony count of negative control×100%

(5) Analysis of results:

TABLE 1

| Antibacterial rates of the polypeptide (SEQ ID NO: 1) of the present invention against the six bacteria | | | | | | |
|---|---|---|---|---|---|---|
| | *Escherichia coli* | *Streptococcus agalactiae* | *Pseudomonas aeruginosa* | *Vibrio fluvialis* | *Aeromonas hydrophila* | *Staphylococcus aureus* |
| 1.0 mg/ml | 100% | 100% | 100% | 100% | 100% | 85% |
| 0.1 mg/ml | 100% | 36% | 100% | 100% | 100% | 26% |
| 0.01 mg/ml | 75% | 3% | 85% | 23% | 62% | 2% |
| 0.001 mg/ml | 6% | 0% | 12% | 3% | 2% | 0% |

As seen from Table 1, the polypeptide having SEQ ID NO: 1 of the present invention has a high antibacterial rate against *Escherichia coli, Vibrio fluvialis, Pseudomonas aeruginosa* and *Aeromonas hydrophila* at low concentrations, indicating that it has an obvious antibacterial effect on the four bacteria. As can be seen from the antibacterial rates in the above table, it has a weak antibacterial effect on *Streptococcus agalactiae* and *Staphylococcus aureus*.

Embodiment 3. Hemolytic Toxicity Tests of the Derivative Peptide on Erythrocytes of Mice and Grass Carp (1) 1 ml of blood of fresh grass carp and BALB/c mice are collected respectively and stored with heparin sodium for anticoagulation.

(2) The fresh plasma solutions obtained in step (1) are centrifuged under 1000 g for 5 minutes, the supernatant is discarded, and red blood cells are collected.

(3) The collected red blood cells are washed 3 times with PBS buffer, centrifuged under 1000 g for 5 minutes each time, and finally resuspended in 5 ml of PBS buffer.

(4) Preparation of peptide solutions of different concentrations: 100 µl of a 256 µM/L interferon-derived polypeptide having SEQ ID NO:1 of the present invention and 256 µM/L human antibacterial peptide LL37 are added to a 96-well plate, respectively, and is subjected to 2-fold dilution, and 3 parallels are prepared for each group.

(5) 50 µl of the prepared red blood cell suspension is uniformly mixed with 50 µl of solutions with different concentrations of the interferon-derived polypeptide or the human antibacterial peptide LL37 dissolved in the PBS, and the mixed solutions are incubated in an incubator at 37° C. for 1 hour. 50 μl PBS+50 μl red blood cell suspension is used as a negative control, and 50 μl of red blood cell suspension+ 50 μl of 0.2% Triton X-100 is used as a positive control.

(6) After 1 hour, the 96-well plate is taken out, and centrifuged under 1000 g for 5 minutes at 4° C.

(7) The supernatant of the above-mentioned centrifuged solutions is taken and placed on a clean 96-well plate again, and then absorbance is measured at 570 nm with a microplate reader.

(8) The average values of all the groups are compared and analyzed. The test is repeated three times.

$$\text{Calculation formula: Hemolysis rate=(absorbance of experimental group−absorbance of negative group)/(absorbance of positive group−absorbance of negative group)×100\%.} \quad (9)$$

(10) It is indicated by hemolytic toxicity analysis that the hemolytic toxicity of the interferon-derived polypeptide having SEQ ID NO:1 of the present invention to red blood cells of mice and grass carp is less than 15% when the concentration of the interferon-derived polypeptide is 128 μM or below; however, the hemolytic toxicity of the human LL37 antimicrobial peptide solutions with the concentration of 64 μM or above is obvious, and its hemolytic toxicity to red blood cells of both mice and grass carp is 50% or higher when the dose concentration is up to 128 μM, indicating that the interferon-derived polypeptide is far less toxic than the human LL37. The experimental results are shown in Table 2.

TABLE 2

Hemolysis rate of the polypeptide having SEQ ID NO: 1 of the present invention and LL37

| Experimental group | Final concentrations of the interferon-derived polypeptide and the antimicrobial peptide LL37 | | | | |
| --- | --- | --- | --- | --- | --- |
| | 8 μM | 16 μM | 32 μM | 64 μM | 128 μM |
| LL37 + red blood cells of grass carp | 5% | 7.6% | 16% | 29% | 62% |
| LL37 + red blood cells of mice | 4.7% | 6.3% | 13% | 21% | 53% |
| Interferon-derived polypeptide + red blood cells of grass carp | 2.6% | 3.2% | 7% | 9% | 11% |
| Interferon-derived polypeptide + red blood cells of mice | 1.7% | 2.3% | 6.3% | 10.2% | 13% |

Embodiment 4

Cytotoxicity test of the interferon-derived polypeptide on human HEK293T cells and grass carp CIK cells:

The MTT method, also known as the MTT colorimetric method, is a method for measuring cell proliferation and cell survival rate. The detection principle is that the sputum acid deoxygenase in the living cell mitochondria can reduce the exogenous MTT to a water-insoluble blue-purple crystalline Formazan which deposits in the cells, while the dead cells have no such function. DMSO can dissolve Formazan in the cells, and through measuring its absorbance by using an enzyme-linked immunosorbent detector at a wavelength of 492 nm, the number of living cells can be reflected indirectly. Within a certain range of the number of cells, the amount of the formed MTT crystal is proportional to the number of cells.

(1) Cell preparation: A human HEK293T cell line and grass carp CIK cell line preserved in liquid nitrogen are resuscitated and cultured in DMEM containing 10% fetal bovine serum under the conditions of 37° C./28° C., 5% CO2, and saturated humidity. The culture solution is changed every other day, and the cell passage is carried out by trypsinization. When 80%-90% of the bottom of the flask is covered with cells, the cells are washed twice with PBS, 2 ml of 0.25% trypsin digestive juice is added, and the degree of digestion is observed under an inverted microscope; when most of the cells are rounded and the cells are in loose connection, it indicates moderate digestion and this process is about 3 minutes; the digestion is terminated by adding a DMEM or MEM medium containing fetal bovine serum, the digestive juice is poured off, and about 3 ml of the cell culture solution is added to thoroughly blow the cells to form a single cell suspension. Finally, the diluted cell suspension is added to a 96-well plate, and 50 μl of the diluted cell suspension is added to each well at a concentration of about $1 \times 10^4$ cells/well.

(2) Drug treatment: After the cells are attached, the medium containing different concentrations of the interferon-derived polypeptide or the human LL37 antimicrobial peptide is separately added. The cell wells without the interferon-derived polypeptide are used as positive control, and the cell well with the interferon-derived polypeptide but without the cells are used as negative control, and the culture is further continued for 24 hours.

(3) Reading: After culture for a certain period of time, 50 μl (5 mg/ml) of MTT is directly added to each well, and after culture for 4 hours, 150 μl of DMSO is added and vibration is carried out for 10 minutes to dissolve the crystal, and the absorbance is then measured at 492 nm by the enzyme-linked immunosorbent detector. The test is repeated three times.

(4) Analysis of the results in Table 3 shows that for the human HEK293T cell line and the grass carp CIK cell line, in the concentration range of the polypeptide having SEQ ID NO: 1 of the present invention being 8-128 μM, the cell survival rate decreases slightly with the increase of the antimicrobial peptide concentration, and the survival rate is higher than 80% when the antimicrobial peptide concentration is up to 128 μM; however, for cells treated with LL37 in the control group, the survival rate of the cells decreases obviously with the increase of LL37 concentration and the survival rate is only 15% when the LL37 concentration is up to 128 μM.

$$\text{Survival rate=(absorbance of experimental group−absorbance of negative group)/(absorbance of positive group−absorbance of negative group)×100\%.} \quad (5)$$

TABLE 3

Survival rates of cells treated with the polypeptide having SEQ ID NO: 1 of the present invention and LL37

| | Final concentrations of the interferon-derived polypeptide and the antimicrobial peptide LL37 | | | | |
| --- | --- | --- | --- | --- | --- |
| | 8 μM | 16 μM | 32 μM | 64 μM | 128 μM |
| LL37 + grass carp CIK | 97% | 87% | 76% | 56% | 15% |
| LL37 + human HEK293 | 98% | 86% | 71% | 51% | 19% |
| Interferon-derived polypeptide + grass carp CIK | 95.4% | 96.7% | 95.2% | 87% | 81% |
| Interferon-derived polypeptide + human HEK293 | 98.3% | 97.2% | 93% | 89% | 83% |

Embodiment 5. Antibacterial Effect of the Interferon-Derived Polypeptide in Mice (1) Test Animal SPF grade BALB/c mice weighed 20±2 g, female, are purchased from the Experimental Animal Center of Huazhong Agricultural University. BALB/c mice are warehoused in the Experimental Animal Research Center of Huazhong Agricultural University. They are kept in metabolic cages, given free access to drinking water and fed with ordinary pellet feed. Breeding environment: humidity (50%±10%), light (12 h-light and 12 h-dark cycle), temperature (23±2°) C. Seven days after the mice are adapted to the breeding conditions, they are divided into the drug-administered group and the control group randomly.

(2) Establishment of a Peritonitis Model

A working solution is prepared by using PBS with a pH of 7.2 as a solvent and is then filtered and sterilized by using a 0.22 μm aqueous microporous filter; the freshly cultured pathogenic *Escherichia coli* is doubly diluted with PBS to 3 concentrations, and each concentration of pathogenic *Escherichia coli* is intraperitoneally injected to infect ten mice. After the injection, the mice are given free access to feed and drinking water, and the deaths are observed and recorded every 6 hours within 48 hours. A peritonitis model is established by selecting the corresponding dose of the 100% mortality group in the mice. The minimum dose of the bacterial solution in which the bacteria causes 100% death of the mice within 48 hours is confirmed by pre-tests. The final minimum dose of 100% mortality in the experiment is $2\times10^7$ CFU/head.

(3) Investigation of Peritonitis Survival Rate

Preparation of a bacterial solution: The bacteria are inoculated into an LB medium and cultured overnight at 37° C.; then a certain amount of the bacterial solution is cultured to a concentration required for the minimum lethal dose.

First, an appropriate drug treatment dose is selected through pre-tests, and an appropriate drug dose concentration is found through 3-5 different drug dose concentration groups. In addition, the toxicity of the drug to mice should be tested so as to preliminarily evaluate the safety of the drug, that is, in the absence of bacterial infection, only the mice are intraperitoneally injected with the interferon-derived polypeptide drug, and the safe dose range is <200 μg/head.

Experimental grouping and processing: The experiment is performed in 6 groups, 10 mice in each group. Each mouse is intraperitoneally injected with a bacterial suspension ($1\times10^8$ CFU/ml, 0.2 ml), and the grouping is as follows:

| Drug-administered group 1 hour after infection: | |
|---|---|
| Control group | Injected with PBS 1 hour after an intraperitoneal injection of the bacteria |
| A | Injected with 25 μg of the interferon-derived peptide 1 hour after an intraperitoneal injection of the bacteria |
| B | Injected with 50 μg of the interferon-derived peptide 1 hour after an intraperitoneal injection of the bacteria |
| C | Injected with 100 μg of the interferon-derived peptide 1 hour after an intraperitoneal injection of the bacteria |
| D | Injected with 200 μg of the interferon-derived peptide 1 hour after an intraperitoneal injection of the bacteria |
| E | Injected with 25 μg of the interferon-derived peptide respectively 1 hour, 3 hours and 5 hours after an intraperitoneal injection of the bacteria |

Mice are given free access to feed and water for 7 consecutive days and the death record is made.

Analysis of experimental results of the protection rate of the derivative peptide (SYEKKINRHFKILKKNLKKK, SEQ ID NO: 1) in FIG. 1 shows that (i) mice injected with 25-200 μg of the interferon-derived polypeptide have a mortality rate of 60%-80%, and the mortality rate of the control group is 100%; (ii) mice with a continuous injection of 25 μg of the interferon-derived polypeptide have a mortality rate of 0; and (iii) mice in the control group all die within 0-48 h, and mice injected with the interferon-derived polypeptide die after 48 h or do not die.

(4) Detection of the Number of Bacteria in the Peritoneal Cavity of Mice with Peritonitis The establishment method and administration of the acute peritonitis model in mice are the same as above. After the mice are infected with the bacteria for 24 hours, 2 ml of normal saline is intraperitoneally injected; then the mice are sacrificed by cervical dislocation, the abdominal cavities are opened, and the livers, spleens, kidneys, brains, lungs, and blood are taken and then ground and diluted; the bacterial solution is uniformly spread on the surface of the LB agar medium and then incubated at 37° C. overnight, and colony counting is performed. Six animals in each group are taken and the average value is determined as the test result.

Analysis of experimental results of the bacterial load of the derivative peptide (SYEKKINRHFKILKKNLKKK, SEQ ID NO: 1) in the different organs in mice as shown in FIGS. 2A to 2F show that, by comparison, the tissue burdens in the experimental group after the injection of the polypeptide are all significantly decreased, where the tissue burdens in blood (FIG. 2F), spleens (FIG. 2E), and livers (FIG. 2D) are decreased by about 1000 times, and the tissue burdens in kidneys (FIG. 2C), brains (FIG. 2B), and lungs (FIG. 2A) are decreased by 10-100 times.

We claim:

1. A polypeptide consisting of SEQ ID NO: 1.

2. A method for inhibiting bacterial growth, comprising preparing a composition comprising a polypeptide consisting of SEQ ID NO:1, and
treating bacteria growth from the bacteria that are selected from the group consisting of drug-resistant *Escherichia coli, Pseudomonas aeruginosa, Staphylococcus aureus, Streptococcus agalactiae, Vibrio fluvialis*, and *Aeromonas hydrophila* with the composition.

3. A method for treating or preventing bacterial infection in a human or animal subject exposed to bacterial infection, comprising
preparing a pharmaceutical composition comprising a polypeptide consisting of SEQ ID NO: 1, and
treating the human or animal subject exposed to bacterial infection with an effective amount of the pharmaceutical composition.

4. The method of claim 3, wherein the bacterial infection is caused by drug-resistant *Escherichia coli, Pseudomonas aeruginosa, Staphylococcus aureus, Streptococcus agalactiae, Vibrio fluvialis*, or *Aeromonas hydrophila*.

* * * * *